United States Patent
Warne et al.

(10) Patent No.: US 7,033,992 B2
(45) Date of Patent: Apr. 25, 2006

(54) FORMULATIONS FOR IL-11

(75) Inventors: Nicholas W. Warne, Andover, MA (US); Rebecca L. Ingram, Nutting Lake, MA (US); Shannon Macmillan, Hollis, NH (US)

(73) Assignee: Genetics Institute LLC, Cambridge, MA (US)

( * ) Notice: Subject to any disclaimer, the term of this patent is extended or adjusted under 35 U.S.C. 154(b) by 555 days.

(21) Appl. No.: 09/971,813

(22) Filed: Oct. 5, 2001

(65) Prior Publication Data

US 2004/0057927 A1    Mar. 25, 2004

Related U.S. Application Data

(63) Continuation of application No. 09/354,390, filed on Jul. 15, 1999, now abandoned.

(51) Int. Cl.
A01N 37/18   (2006.01)
C07K 14/00   (2006.01)

(52) U.S. Cl. .......................... 514/2; 530/351

(58) Field of Classification Search ............... 514/2; 530/351; 435/4, 69.6
See application file for complete search history.

(56) References Cited

U.S. PATENT DOCUMENTS

| | | | |
|---|---|---|---|
| 5,215,895 A | 6/1993 | Bennett et al. | |
| 5,270,181 A | 12/1993 | McCoy et al. | |
| 5,292,646 A | 3/1994 | McCoy et al. | |
| 5,371,193 A * | 12/1994 | Bennett et al. | 530/351 |
| 5,430,064 A | 7/1995 | Hirsch et al. | 514/554 |
| 5,582,821 A | 12/1996 | Kaye | 424/85.2 |
| 5,679,339 A * | 10/1997 | Keith et al. | 424/85.2 |
| 5,700,664 A | 12/1997 | Yang et al. | |
| 5,885,962 A | 3/1999 | Lu | 514/12 |
| 5,948,402 A | 9/1999 | Keith et al. | 424/85.2 |
| 5,958,401 A | 9/1999 | Keith et al. | |
| 6,066,317 A | 5/2000 | Yang et al. | 424/85.2 |
| 6,096,873 A * | 8/2000 | Schaefer et al. | 530/399 |
| 6,270,757 B1 | 8/2001 | Warne | 424/85.2 |

FOREIGN PATENT DOCUMENTS

| WO | WO91/07495 | 5/1991 |
|---|---|---|
| WO | WO92/04455 | 3/1992 |

OTHER PUBLICATIONS

Siadati and Sarr.(1998). Role of extrinsic innervation in release of motilin and patterns of upper gut canine motility. *J. Gastrointest. Sur.* 2(4): 363-72.

Luiking, et al.(1998). Motilin induces gall bladder emptying and antral contractions in the fasted state in humans. *Gut* 42(6): 830-5.

Depoortere, et al. (1997). Distribution and subcellular localization of motilin binding sites in the rabbit brain. *Brain Res.* 777(1-2):103-9.

Van Assche, et al. (1997). Concentration-dependent stimulation of cholinergic motor nerves or smooth muscle by [Nle 13]motilin in the isolated rabbit gastric antrum. *Eur. J. Pharmacol.* 377(2-3):267-74.

Tomita, et al. (1997), The role of motilin and cisapride in the enteric nervous system of the lower esophageal sphincter in humans. *Surg. Today.* 27(11):985-92.

Boivin, et al. (1997). Neural mediation of the motilin motor effect on the human antrum. *Am. J. Physiol.* 272(1 Pt 1): G71-6.

Yokoyama, et al. (1995). Recovery of gastrointestinal motility from post-operative ileus in dogs: effects of Leu 13-motilin (KW-5139) and prostaglandin F2 alpha. *Neurogastroenterol. Motil.* 7(4): 199-210.

De Clercq, et al. (1998). Motilin in human milk: identification and stability during digestion. *Life Sci.* 63(22): 1993-2000.

Ordaz-Jimenez, et al. (1998). [Gastrointestinal hormones during minimal enteral feeding of sick premature infants] *Rev. Invest. Clin.* 50(1):37-42. (Spanish w/ English abstract).

Jadcheria, et al. (1997). Regulation of migrating motor complexes by motilin and pancreatic polypeptide in human infants. *Pediatr. Res.* 42(3): 365-9.

Omura, et al. (1987). Macrolides with gastrointestinal motor stimulating activity. *J Med Chem.* 30(11): 1941-3.

(Continued)

*Primary Examiner*—Bradley L. Sisson
(74) *Attorney, Agent, or Firm*—Ivor R. Elrifi; David E. Johnson; Mintz Levin

(57) ABSTRACT

Provided by the present invention are novel compositions and methods for obtaining concentrated preparations of IL-11 and formulations of IL-11 suitable for storage and administration.

24 Claims, No Drawings

OTHER PUBLICATIONS

Weich, et al (1997). Recombinant human interleukin-11 directly promotes megakaryocytopoiesis in vitro. *Blood.* 90(10): 3893-902.

Orazi, et al. (1996). Effects of recombinant human interleukin-11 (Neumega rhIL-11 growth factor) on megakaryocytopoiesis in human bone marrow. *Exp. Hematol.* 24(11): 1289-97.

Du, et al. (1997). Protective effects of interleukin-11 in a murine model of ischemic bowel necrosis. *Am. J. Physiol.* 272(3 Pt 1): G545-52.

Orazi, et al. (1996). Interleukin-11 prevents apoptosis and accelerates recovery of small intestinal mucosa in mice treated with combined chemotherapy and radiation. *Lab Invest.* 75(1): 33-42.

Keith, et al. (1994). "IL-11, a pleiotropic cytokine: exciting new effects of IL-11 on gastrointestinal mucosal biology." *Stem Cells.* 12 (Suppl 1):79-90.

Qiu, et al.. (1996). Protection by recombinant human interleukin-11 against experimental TNB-induced colitis in rats. *Dig. Dis. Sci.*41(8): 1625-30.

Hill, et al. (1998). Interleukin-11 promotes T cell polarization and prevents acute graft-versus-host disease after allogeneic bone marrow transplantation. *J. Clin. Invest.* 102(1): 115-23.

Redlich, et al. (1996). IL-11 enhances survival and decreases TNF production after radiation-induced thoracic injury. *J. Immunol.* 157(4): 1705-10.

Waxman, et al. (1998). Targeted lung expression of interleukin-11 enhances murine tolerance of 100% oxygen and diminishes hyperoxia-induced DNA fragmentation. *J Clin Invest.* 101(9):1970-82.

Leng and Elias (1997). Interleukin-11 inhibits macrophage interleukin-12 production. *J. Immunol.* 159(5):2161-8.

Trepicchio, et al. (1997). IL-11 regulates macrophage effector function through the inhibition of nuclear factor-kappaB. *J. Immunol.* 159(11): 5661-70.

Trepicchio, et al. (1996). Recombinant human IL-11 attenuates the inflammatory response through down-regulation of proinflammatory cytokine release and nitric oxide production. *J. Immunol.* 157(8): 3627-34.

Taga and Kishimoto (1997). Gp130 and the interleukin-6 family of cytokines. *Annu. Rev. Immunol.* 15:797-819.

Zhang, et al. (1994). Ciliary neurotropic factor, interleukin 11, leukemia inhibitory factor, and oncostatin M are growth factors for human myeloma cell lines using the interleukin 6 signal transducer gp130. *J. Exp. Med.* 179(4):1337-42.

Yang and Yin. (1995). Interleukin (IL)-11—mediated signal transduction. *Ann. NY Acad. Sci.* 762: 31-41.

Nandurkar, et al. (1996). The human IL-11 receptor requires gp130 for signalling: demonstration by molecular cloning of the receptor. *Oncogene.* 12(3):585-93.

Miyatake, et al. (1998). Complement-fixing elicited antibodies are a major component in the pathogenesis of xenograft rejection. *J. Immunol.* 160(8): 4114-23.

Yin, et al. (1994). Identification of a 130-kilodalton tyrosine-phosphorylated protein induced by interleukin-11 as JAK2 tyrosine kinase, which associates with gp130 signal transducer. *Exp. Hematol.* 22(5): 467-72.

Wang, et al. (1995). Interleukin-11 induces complex formation of Grb2, Fyn, and JAK2 in 3T3L1 cells. *J. Biol. Chem.* 270(47): 27999-8002.

Lutticken, et al. (1994). Association of transcription factor APRF and protein kinase Jak1 with the interleukin-6 signal transducer gp130. *Science* 263(5143): 89-92.

Hemmann, et al. (1996). Differential activation of acute phase response factor/Stat3 and Stat1 via the cytoplasmic domain of the interleukin 6 signal transducer gp130. *J. Biol. Chem.* 27(22): 12999-3007.

Zhong, et al. (1994). Stat3: a STAT family member activated by tyrosine phosphorylation in response to epidermal growth factor and interleukin-6. *Science.* 264(5155): 95-8.

Akira (1997). IL-6-regulated transcription factors. *Int. J. Biochem. Cell Biol.* 29(12):1401-18.

Zhang, et al. (1995). Requirement of serine phosphorylation for formation of STAT-promoter complexes. *Science* 267(5206): 1990-4.

Boulton, et al. (1995). STAT3 activation by cytokines utilizing gp130 and related transducers involves a secondary modification requiring an H7-sensitive kinase. *Proc. Natl. Acad. Sci. USA.* 92(15): 6915-9.

Adunyah, et al. (1995). Interleukin-11 induces tyrosine phosphorylation, and c-jun and c-fos mRNA expression in human K562 and U937 cells. *Ann. NY Acad. Sci.* 766: 296-9.

Yin and Yang (1994). Mitogen-activated protein kinases and ribosomal S6 protein kinases are involved in signaling pathways shared by interleukin-11, interleukin-6, leukemia inhibitory factor, and oncostatin M in mouse 3T3-L1 cells. *J. Biol.Chem.* 269(5): 3731-8.

Paul, et al. (1990). Molecular cloning of a cDNA encoding interleukin 11, a stromal cell-derived lymphopoietic and hematopoietic cytokine. *Proc. Natl. Acad. Sci. USA* 87(19):7512-6

Balkwill and Burke (1989). The cytokine network. *Immunol Today* 10(9): 299-304.

Wong and Clark (1988). Multiple actions of interleukin 6 within a cytokine network. *Immunol. Today.* (5): 137-9.

Clark and Kamen (1987). The human hematopoietic colony-stimulating factors. *Science.*236(4806):1229-37.

Jacobs, et al. (1970). Characteristics of a human diploid cell designated MRC-5, *Nature* 227(254): 168-70.

Ikebuchi, et al. (1988). Synergistic factors for stem cell proliferation: further studies of the target stem cells and the mechanism of stimulation by interleukin-1, interleukin-6, and granulocyte colony-stimulating factor. *Blood* 72(6): 2007-14.

Bruno, et al. (1991). Effects of recombinant interleukin 11 on human megakaryocyte progenitor cells. *Exp. Hematol.* 19(5): 378-81.

Du and Williams (1994). Interleukin-11: a multifunctional growth factor derived from the hematopoietic microenvironment. *Blood.* 83(8): 2023-30.

Yin, et al.. (1992). Enhancement of in vitro and in vivo antigen-specific antibody responses by interleukin 11. *J. Exp. Med.* 175(1): 211-6.

Barton, et al. (1996). Interleukins 6 and 11 protect mice from mortality in a staphylococcal enterotoxin-induced toxic shock model. *Infect. Immun.* 64(3):714-8.

Castagliuolo, et al. (1997). IL-11 inhibits Clostridium difficile toxin A enterotoxicity in rat ileum. *Am. J. Physiol.* 273(2 Pt 1): G333-41.

Liu, et al. (1996). Trophic effects of interleukin-11 in rats with experimental short bowel syndrome. *J. Pediatr. Surg.* 31(8): 1047-51.

Fiore, et al. (1998). Comparison of interleukin-11 and epidermal growth factor on residual small intestine after massive small bowel resection. *J. Pediatr. Surg.* 33(1): 24-9.

Schindel, et al. (1997). Interleukin-11 improves survival and reduces bacterial translocation and bone marrow suppression in burned mice. *J. Pediatr. Surg.* 32(2): 312-5.

Musashi, et al. (1991). Synergistic interactions between interleukin-11 and interleukin-4 in support of proliferation of primitive hematopoietic progenitors of mice. *Blood.* 78(6): 1448-51.

Burstein, et al. (1992). Leukemia inhibitory factor and interleukin-11 promote maturation of murine and human megakaryocytes in vitro. *J. Cell. Physiol.* 153(2): 305-12.

Baumann and Schendel. (1991). Interleukin-11 regulates the hepatic expression of the same plasma protein genes as interleukin-6. *J. Biol. Chem.* 266(30): 20424-7.

Kawashima, et al. (1991). Molecular cloning of cDNA encoding adipogenesis inhibitory factor and identity with interleukin-11. *FEBS Lett.* 283(2): 199-202.

Fann and Patterson. (1994). Neuropoietic cytokines and activin A differntially regulate the phenotype of cultured sympathetic neurons. *Proc. Natl. Acad. Sci. USA.* 91(1): 43-7.

Yin, et al. (1993). Involvement of IL-6 signal transducer gp130 in IL-11-mediated signal transduction. *J. Immunol.* 151(5): 2555-61.

Hibi, et al. (1990). Molecular cloning and expression of an IL-6 signal tranducer, gp130. *Cell* 63(6): 1149-57.

Omura, et al. (1985). Gastrointestinal motor-stimulating activity of macrolike antibiotics and the structure-activity relationship. *J. Antibiot.* (Tokyo) 38(11): 1631-2.

Depoortere, et al. (1998). *Am. Gastroenterology Soc.* (New Orlenas, LA, May 16-22, 1998).

Opal, et al. (1998). Recombinant human interleukin-11 in experimental Pseudomonas aeruginosa sepsis in immunocompromised animals. *J. Infect. Dis.* 178(4): 1205-8.

Girasole, et al. (1994). Interleukin-11: a new cytokine critical for osteoclast development. *J. Clin. Invest.* 93(4):1516-24.

Keith, et al. (1995). *Gastroenterology* 108(4): A846.

Keith, et al. (1994). *Gastroenterology* 106(4 part 2): A708.

Opal, et al. (1995). *Blood* 86(10): 498A.

Sonis, et al. (1995). Alteration in the frequency, severity and duration of chemotherapy-induced mucositis in hamsters by interleukin-11. *Eur. J. Cancer B. Oral Oncol.* 31B(4): 261-6.

Leonard, et al. (1995). Prevention of experimental autoimmune encephalomyelitis by antibodies against interleukin 12. *J. Exp. Med.* 181(1): 381-6.

Scofield, et al. (1993). A hypothesis for the HLA-B27 immune dysregulation in spondyloarthropathy: contributions from enteric organisms, B27 structure, peptides bound by B27, and convergent evolution. *Proc. Natl. Acad. Sci. USA.* 90(20): 9330-4.

Hammer, et al. (1990). Spontaneous inflammatory disease in transgenic rats expressing HLA-B27 and human beta 2m: an animal model of HLA-B27-associated human disorders. *Cell.* 63(5): 1099-112.

Sonis, et al. (1995). *Proc. Am. Assoc. Cancer Res.* 36: 368.

Remington (1995). *The Science and Pratice of Pharmacy* vol. 2: 1403-1407 and 1626-1627. (Mack Publishing—19th edition).

* cited by examiner

FORMULATIONS FOR IL-11

This is a continuation of application Ser. No. 09/354,390, filed Jul. 15, 1999, now abandoned.

FIELD OF INVENTION

The present invention relates generally to novel formulations comprising interleukin-11 ("IL-11").

BACKGROUND OF THE INVENTION

Interleukin 11 ("IL-11") is a pleiotropic cytokine that stimulates a variety of hematopoietic and immune functions, such as primitive lymphohematopoietic progenitor cells and other hematopoietic growth factors which stimulate the proliferation and maturation of megakaryocytes. IL-11 is described in detail in International Application PCT/US90/06803, published May 30, 1991, as well as in U.S. Pat. No. 5,215,895; issued Jun. 1, 1993. A cloned human IL-11 was previously deposited with the American Type Culture Collection (ATCC), 10801 University Blvd., Manassas, Va., on Mar. 30, 1990 under ATCC No. 68284. Moreover, as described in U.S. Pat. No. 5,270,181, issued Dec. 14, 1993, and U.S. Pat. No. 5,292,646, issued Mar. 8, 1994, IL-11 may also be produced recombinantly as a fusion protein with another protein.

It is desirable to have concentrated forms of bulk protein, e.g. IL-11, which, in turn, may be stored and which are suitable for further manufacture of finished dosage forms of protein. Typically, a purification process for a protein results in purified, concentrated protein. This concentrated protein, also known as bulk protein, may be in a formulation buffer. Bulk protein, typically at a concentration of about 0.1 to at least 20 mg/ml, can then be shipped frozen to a fill/finish facility where it is diluted to an appropriate concentration and filled into vials. These diluted samples can be lyophilized, i.e., freeze-dried. The lyophilized samples may be kept in long-term storage and reconstituted at a later time by adding a suitable administration diluent just prior to patient use.

Protein stability can be affected inter alia by such factors as ionic strength, pH, temperature, repeated cycles of freeze/thaw and exposures to shear forces. Active protein may be lost as a result of physical instabilities, including denaturation and aggregation (both soluble and insoluble aggregate formation), as well as chemical instabilities, including, for example, hydrolysis, deamidation and oxidation, to name just a few. For a general review of stability of protein pharmaceuticals, see, for example, Manning, et al., Pharmaceutical Research 6:903–918 (1989).

While the possible occurrence of protein instabilities is widely appreciated, it is impossible to predict particular instability problems of a particular protein. Any of these instabilities can result in the formation of a protein, protein by-product, or derivative having lowered activity, increased toxicity, and/or increased immunogenicity. Also, IL-11 has a tendency to form soluble high molecular weight aggregates which can interfere with product quality and effectiveness in use. Thus, the safety and efficacy of any pharmaceutical formulation of a protein is dependent upon its stability.

In addition to stability considerations, one generally selects excipients which are or will meet with the approval of various world-wide medical regulatory agencies. The solution should be isotonic and the pH in a physiologically suitable range. The choice and amount of buffer used is important to achieve and maintain the desired pH range.

Ideally, formulations should also be stable for IL-11 bulk storage in high concentration ($\geq$20 mg/ml, for example) which allows for relatively small volumes for fill/finish at the appropriate dose and also allows for alternate methods of administration which may require high protein concentration, e.g., sub cutaneous administration. Accordingly, there continues to exist a need in the art for methods for monitoring IL-11 protein stability (and maintaining activity levels) during the concentration process and the lyophilization process, as well as providing stable formulations during prolonged storage.

BRIEF SUMMARY OF THE INVENTION

One aspect of the present invention provides novel compositions and methods for providing concentrated preparations of IL-11, useful as drug product. These compositions, either frozen, liquid, or lyophilized (preferably lyophilized), comprise IL-11, a bulking agent, and a cryoprotectant, and optionally include a polysorbate, methionine, and a buffering agent which maintains the pH of said composition in the range of from about 6.0 to about 8.0.

Another aspect of the present invention provides compositions comprising formulations of IL-11 of a concentration useful for administration in final dosage forms.

Preferably the bulking agent is selected from the group consisting of glycine, mannitol, and NaCl, and combinations thereof, most preferably glycine. When glycine is used, the glycine is present at a concentration of about 1 mM to about 1 M, preferably at a concentration of about 100 to about 400 mM, and most preferably at a concentration of about 300 mM.

Preferably, the cryoprotectant is selected from the group consisting of sucrose, trehalose, hydroxyethyl starch and combinations thereof, most preferably sucrose. Preferably, the cryoprotectant comprises about 0.5 to about 5% of the composition. When sucrose is used, a preferred concentration is from about 0.5 to about 2%, most preferably about 1%.

Preferably, the polysorbate is selected from the group consisting of TWEEN-20® (polysorbate-20) and TWEEN-80® (polysorbate-80), most preferably TWEEN-20®. In certain embodiments, the polysorbate is present at a concentration of about 0.001 to 0.1%, preferably at a concentration of about 0.005 to about 0.1%, most preferably at a concentration of about 0.02%. A plurality of polysorbates may also be used.

In certain embodiments, the composition comprises methionine, preferably at a concentration of about 0.001 mM to about 1 M, more preferably at a concentration of about 1 to about 100 mM, and most preferably at a concentration of about 10 mM.

In preferred embodiments, the buffering agent maintains the pH of said composition in the range of from about 6.0 to about 8.0, most preferably at about 7.0. Preferred buffering agents are selected from the group consisting of phosphate, histidine, succinate, Tris, and diethanolamine, with phosphate (particularly the sodium and potassium salts thereof) and histidine being most preferred. The buffering agent may range in concentration from about 1 mM to about 100 mM, preferably from about 5 mM to about 40 mM, with 10 mM most preferred for sodium phosphate and 20 mM most preferred for histidine.

Preferably the protein is present at a concentration of about 1 µg/ml to about 20 mg/ml, more preferably at about 1 to about 10 mg/ml, most preferably at a concentration of about 1 to about 5 mg/ml.

Particularly preferred embodiments of the invention comprise about 1 to about 5 mg/ml IL-11, about 300 mM glycine, about 1% sucrose, and have a pH of about 7.0. Particularly preferred embodiments also optionally comprise about 0.02% polysorbate and about 10 mM methionine.

DETAILED DESCRIPTION OF THE INVENTION

As used herein, the terms lyophilization, lyophilized, and freeze-dried include but are not limited to processes including "freezing" a solution followed by "drying," optionally in vacuo. As used herein, the term "bulking agent" comprises agents which provide good lyophilized cake properties, which help the protein overcome various stresses (shear/freezing for example) associated with the lyophilization process, and which help to maintain protein activity levels. Exemplary bulking agents include, but are not limited to, glycine, mannitol, NaCl, and the like. These agents contribute to the tonicity of the formulations. Cryoprotectants also contribute to the tonicity. The term "cryoprotectants" generally includes agents which provide stability to the protein from freezing-induced stresses; however, the term also includes agents that provide stability, e.g. to bulk drug formulations during storage from non-freezing-induced stresses. Exemplary cryoprotectants include saccharides such as sucrose and mannitol, as well as including surfactants such as polysorbates, polyols and polyethyleneglycol, and the like. The term "cryoprotectant" includes agents that provide stability to the protein during water removal from the system during the drying process, presumably by maintaining the proper conformation of the protein through hydrogen bonding. Cryoprotectants can also have lyoprotectant effects; therefore, the terms "cryoprotectant" and "lyoprotectant" are used interchangeably herein. The present inventors have discovered that stabilization of proteins by cryoprotectants can be further increased by using a combination of cryoprotectants, such as sucrose and a polysorbate.

As used herein, the term "antioxidant" comprises agents which inhibit oxidation of $Met^{58}$ within IL-11, thereby preventing protein degradation and helping to maintain protein activity levels. Exemplary antioxidants include, but are not limited to, thioethers such as methionine and methylthioethane. These agents contribute to the stability of the protein, presumably by providing an alternative substrate for oxidative reactions in solution.

The term "buffering agent" encompasses those agents which maintain the solution pH in an acceptable range prior to lyophilization and may include phosphate (sodium or potassium), histidine, succinate, Tris (tris (hydroxymethyl) aminomethane), diethanolamine, and the like. The upper concentration limits are generally higher for "bulk" protein than for "dosage" protein forms as is readily appreciated by one skilled in the art. For example, while buffer concentrations can range from several millimolar up to the upper limit of their solubility, e.g., succinate could be as high as 200 mM, one skilled in the art would also take into consideration achieving/maintaining an appropriate physiologically suitable concentration. Percentages are weight/weight when referring to solids and weight/volume when referring to liquids. The term "isotonic," 300±50 mOsM, is meant to be a measure of osmolality of the protein solution after reconstitution; reconstitution is typically with water for injection (WFI). Maintaining physiological osmolality is important for the dosage formulations. However, for bulk formulations, much higher concentrations can be effectively utilized as long as the solution is made isotonic prior to use. The term "excipients" includes pharmaceutically acceptable reagents to provide good lyophilized cake properties (bulking agents) as well as provide lyoprotection and cryoprotection of the protein, maintenance of pH, and proper conformation of the protein during storage so that substantial retention of biological activity (protein stability) is maintained. Preferably, the combined concentration of the excipients provides a combined osmolality of about 250 to about 350 milliosmol (mOsm) per kg, more preferably about 300 mOsm/kg.

Applicants find that some of the chemical instability of IL-11 is a result of hydrolysis between $Asp^{133}$ and $Pro^{134}$. Also, deamidation of $Asn^{49}$ to $Asp^{49}$ is detected. In addition, oxidation of $Met^{58}$ is observed. All of these chemical reactions are evidence of IL-11 protein chemical instability. IL-11 is also subject to certain physical instabilities including a dimerization process, as well as aggregate formation. The chemical instability of IL-1, as well as the use of glycine and a buffering agent to improve the stability, is disclosed in copending application U.S. Ser. No. 08/230,982, filed Apr. 21, 1994, which is hereby incorporated by reference in its entirety herein.

According to the present invention, the addition of a bulking agent such as glycine, a cryoprotectant such as sucrose and/or a polysorbate such as TWEEN-20® (polysorbate-20) acts to prevent aggregation of IL-11 and protects IL-11 from the harmful effects of shearing and freezing. This in turn increases the ability to handle the protein and provides enhanced shelf-life for IL-11 products. Moreover, according to the present invention, the addition of an antioxidant such as a thioether (e.g., methionine) reduces the oxidation rate of $Met^{58}$, presumably through a competitive redox mechanism.

Interleukin 11 is a pleiotropic cytokine that stimulates primitive lymphohematopoietic progenitor cells and synergizes with other hematopoietic growth factors to stimulate the proliferation and maturation of megakaryocytes. IL-11 is described in detail in International Application PCT/US90/06803, published May 30, 1991, as well as in U.S. Pat. No. 5,215,895; issued Jun. 1, 1993. A cloned human IL-11 was previously deposited with the American Type Culture Collection (ATCC), 10801 University Blvd., Manassas, Va., on Mar. 30, 1990 under ATCC No. 68284. Moreover, as described in U.S. Pat. No. 5,270,181, issued Dec. 14, 1993, and U.S. Pat. No. 5,292,646, issued Mar. 8, 1994, IL-11 may also be produced recombinantly as a fusion protein with another protein. IL-11 can be produced in a variety of host cells by resort to now conventional genetic engineering techniques. In addition, IL-11 can be obtained from various cell lines, for example, the human lung fibroblast cell line, MRC-5 (ATCC Accession No. CCL 171), and Paul et al., the human trophoblastic cell line, TPA30-1 (ATCC Accession No. CRL 1583). A cDNA encoding human IL-11, as well as the deduced amino acid sequence (amino acids 1 to 199), is described in Proc. Natl. Acad. Sci. USA 87:7512 (1990). U.S. Pat. No. 5,292,646, supra, describes a des-Pro form of IL-11 in which the N-terminal proline of the mature form of IL-11 (amino acids 22–199) has been removed (amino acids 23–199). As is appreciated by one skilled in the art, any form of IL-11 which retains IL-11 activity, such as variants through the substitution or deletion of amino acids, analogs and derivatives of IL-11, is useful according to the present invention. The disclosure of each of the above publications is hereby incorporated by reference for the contents thereof.

In addition to recombinant techniques, IL-11 may also be produced by known conventional chemical synthesis. Methods for constructing the polypeptides useful in the present invention by synthetic means are known to those of skill in the art. The synthetically constructed cytokine polypeptide sequences, by virtue of sharing primary, secondary, or tertiary structural and conformational characteristics with the natural cytokine polypeptides are anticipated to possess biological activities in common therewith. Such synthetically constructed cytokine polypeptide sequences or fragments thereof, which duplicate or partially duplicate the functionality thereof may also be used in the compositions of this invention. Thus, they may be employed as biologically active or immunological substitutes for the natural, purified cytokines useful in the present invention.

Modifications in the protein, peptide or DNA sequences of these cytokines or active fragments thereof may also produce proteins which may be employed in the compositions of this invention. Such modified cytokines can be made by one skilled in the art using known techniques. Modifications of interest in the cytokine sequences, e.g., the IL-11 sequence, may include the replacement, insertion or deletion of one or more selected amino acid residues in the coding sequences. Mutagenic techniques for such replacement, insertion or deletion are well known to one skilled in the art. (See, e.g., U.S. Pat. No. 4,518,584.)

Other specific mutations of the sequences of the cytokine polypeptides which may be useful therapeutically as described herein may involve, e.g., the insertion of one or more glycosylation sites. An asparagine-linked glycosylation recognition site can be inserted into the sequence by the deletion, substitution or addition of amino acids into the peptide sequence or nucleotides into the DNA sequence. Such changes may be made at any site of the molecule that is modified by addition of O-linked carbohydrate. Expression of such altered nucleotide or peptide sequences produces variants which may be glycosylated at those sites.

Additional analogs and derivatives of the sequence of the selected cytokine which would be expected to retain or prolong its activity in whole or in part, and which are expected to be useful in the present invention, may also be easily made by one of skill in the art. One such modification may be the attachment of polyethylene glycol (PEG) onto existing lysine residues in the cytokine sequence or the insertion of one or more lysine residues or other amino acid residues that can react with PEG or PEG derivatives into the sequence by conventional techniques to enable the attachment of PEG moieties.

Additional analogs of these selected cytokines may also be characterized by allelic variations in the DNA sequences encoding them, or induced variations in the DNA sequences encoding them. It is anticipated that all analogs disclosed in the above-referenced publications, including those characterized by DNA sequences capable of hybridizing to the disclosed cytokine sequences under stringent hybridization conditions or non-stringent conditions (Sambrook et al., Molecular Cloning. A Laboratory Manual, 2d edit., Cold Spring Harbor Laboratory, New York (1989)) will be similarly useful in this invention.

Also considered as derivatives useful in these methods are fusion molecules, prepared by fusing the sequence or a biologically active fragment of the sequence of one cytokine to another cytokine or proteinaceous therapeutic agent, e.g. IL-11 fused to IL-6 (see, e.g., methods for fusion described in PCT/US91/06186 (WO92/04455), published Mar. 19, 1992). Alternatively, combinations of the cytokines may be administered together according to the method.

Thus, where in the description of the compositions of this invention IL-11 is mentioned by name, it is understood by those of skill in the art that IL-11 encompasses the protein produced by the sequences presently disclosed in the art, as well as proteins characterized by the modifications described above yet which retain substantially similar activity.

The following examples illustrate practice of the invention. These examples are for illustrative purposes only and are not intended in any way to limit the scope of the invention claimed. Example 1 shows the benefits of adding sucrose to rhIL-11 formulations. Example 2 describes the effects of polysorbate on shearing of IL-11. Example 3 describes the effects of L-methionine on the oxidation of IL-11 in liquid formulations. Example 4 describes the effects of L-methionine on the oxidation of IL-11 in wet granulation tablets. Example 5 describes the effects of L-methionine and polysorbate on the stability of enteric coated rhIL-11 multiparticulate pellets.

EXAMPLES

Example 1

Effect of Sucrose

The effects of sucrose on the stability of lyophilized recombinant human interleukin-11 (rhIL-11) were examined in two stability studies. First, a 26-week study of rhIL-11 in a composition comprising 10 mM sodium phosphate, 300 mM glycine, pH 7.0 (referred to herein as base formulation), was examined with and without 1% sucrose at both 1 mg and 5 mg dosage forms. Samples were aseptically filled into vials and lyophilized, then incubated at 4° C., 30° C., and 40° C. Second, an 34-week study of rhIL-11 in the base formulation (10 mM sodium phosphate, 300 mM glycine, pH 7.0) was examined with no sucrose at 2 and 5 mg/mL and with 1% sucrose at 0.5, 1.0, and 2.0 mg/mL. Samples were aseptically filled into vials and lyophilized. They were then incubated at 4° C., 25° C., and 40° C. Samples were analyzed in both studies periodically by acidic reversed-phase HPLC.

The results of acidic reversed-phase HPLC analysis of 1 mg/vial lyophilized rhIL-11 dosage form formulated with and without sucrose and incubated for 26 weeks at 40° C. were compared. The samples were reconstituted with water and injected onto a poros R1/H column (4.6 mm ID×100 mm L) at ambient temperature at a load of 64 µg. The mobile phase was 0.1% TFA in water with a linear gradient of acetonitrile. This method was run on a Waters Alliance HPLC system detecting at 214 nm.

The results of acidic reversed-phase HPLC analysis of 5 mg/vial lyophilized rhIL-11 dosage form formulated with and without sucrose and incubated for 26 weeks at 40° C. were compared. The text above outlines the reversed-phase HPLC method used.

The results of acidic RP-HPLC analysis of lyophilized rhIL-11 at 2 and 5 mg/vial formulated without sucrose and 0.5, 1.0, and 2.0 mg/vial formulated with 1% sucrose and incubated for 34 weeks at 40° C. were compared. The text above outlines the reversed-phase HPLC method used.

In summary, the 40° C. RP-HPLC data from both studies show that sucrose added to the lyophilized rhIL-11 formulation (at 1, 2, and 5 mg/vial) is beneficial in reducing the amount of aggregate generated on stability.

Example 2

Effect of Polysorbate

The effect of polysorbate-20 on the stability of liquid rhIL-11 was examined in a short-term shaking study. rhIL-11 in the 10 mM sodium phosphate, 300 mM glycine, pH 7.0 composition (base formulation) was examined with and without polysorbate-20 by filling 1 mL rhIL-11 solution (at 4.8 mg/mL) into 2 mL tubing vials with 0, 0.005, 0.01, and 0.02% polysorbate-20. The vials were stoppered and crimped and secured horizontally on a flatbed gel shaker. Duplicate vials were shaken at approximately 120 RPM for the following periods: 0, 1, 2, 4, 8, 16, and 24 hours. At the appropriate timepoint, samples were removed for analysis by light scattering and SEC-HPLC.

Light scattering results of liquid rhIL-11 after shaking for 16 hours in formulations with and without polysorbate-20 were compared. Light scattering was performed using quartz cuvettes in a Hitachi UV/Vis Spectrophotometer where $l=320$ nm.

Results of liquid rhIL-11 after shaking for 16 hours in formulations with and without polysorbate-20. SEC-HPLC was performed using a Toso Haas TSK2000SW$_{XL}$ column (7.8 mm ID×300 mm L) and was run isocratically at 1.0 mL/min. using a 50 mM MES, 0.5M NaCL, 0.1 mM glycine, pH 6.0 mobile phase were compared. The method was run on a Waters HPLC system detecting at 225 nm using a 30 μg column load.

In summary, the 16 hour shaking data show that the addition of polysorbate-20 to the rhIL-11 liquid formulation benefits the stability by significantly reducing the light scattering at 320 nm and % rhIL-11 multimer generated.

Example 3

Effect of L-Methionine on IL-11 Formulations

L-Methionine is believed to protect the methionine residues of IL-11 from oxidation by acting as a scavenger for the oxidizing species. Several experiments were performed which determined that 10 mM methionine was an appropriate and adequate concentration to minimize the oxidation of Met58 within IL-11 (data not shown).

To examine the benefit of L-methionine in the presence of polysorbates, which contain varied levels of oxidizing species such as hydrogen peroxide, IL-11 was aseptically prepared as liquid and lyophilized dosage forms at two concentrations (0.2 mg/mL and 1.0 mg/mL) in formulations with or without 10 mM methionine. Up to 10 different sources of polysorbate, from a variety of vendors, were added to each formulation at a concentration of 0.02% (v/v). The 1 mL samples were incubated at 2–8 EC (data not shown) and at 40 EC.

The stability of liquid IL-11 after 8 weeks at 40 EC in formulations with and without 10 mM methionine were compared. The stability of lyophilized IL-11 after 8 weeks at 40 EC in formulations with and without 10 mM methionine were also compared. Levels of Met58 oxidation were monitored by reversed-phase high-performance liquid chromatography using a Poros R1/H column and a mobile phase of 0.1% TFA in water with a gradient of acetonitrile. Detection was at 214 nm.

The data demonstrate that the addition of 10 mM methionine reduces the level of Met58 oxidation within IL-11. Further, as the protein concentration is varied from 0.2 mg/mL to 1.0 mg/mL, the level of oxidation within the protein decreases with increased protein concentration. This is consistent with concept that the degree of methionine oxidation is dependent on the level of the substrate (methionine) available to the oxidizing species. The conclusion of this experiment is that 10 mM methionine dramatically reduces the level of Met58 oxidation within IL-11.

Example 4

Effect of L-Methionine on IL-11 Tablets

The effect of methionine in rhIL-11 tablet formulations was examined in this 4 week stability study. rhIL-11 tablets were prepared (2.5 mg active/tablet) with or without 10 mM methionine and incubated at 4° C., 25° C., and 40° C. in HDPE bottles for 0, 2, and 4 weeks. Samples were crushed and extracted overnight using a 100 mM sodium phosphate, 300 mM glycine, 0.02% polysorbate-80, 10 mM methionine, pH 7.0 buffer at ambient temperature on a flatbed gel shaker set at low speed. Samples were analyzed at each timepoint by reversed-phase HPLC.

The stability results for rhIL-11 tablets incubated at 40° C. by RP-HPLC for detecting percent (%) oxidized methionine[58] species in formulations with and without methionine were compared. The samples were injected onto a poros R1/H column (4.6 mm ID×100 mm L) that was incubated at 40° C. at a load of 8 μg. The mobile phase was 0.1% TFA in water with a linear gradient of acetonitrile. This method was run on a Waters Alliance HPLC system detecting at 214 nm.

In summary, the addition of methionine to the rhIL-11 tablet formulation reduces the amount of methionine[58] oxidation. This confirms that methionine benefits the rhIL-11 formulation as an antioxidant.

Example 5

Effect of L-Methionine and Polysorbate on IL-11 Multiparticulates

The effect of methionine and polysorbate-80 in rhIL-11 multiparticulate formulations was examined in this 2-month stability study. rhIL-11 multiparticulates were prepared (1 mg active/100 mg multiparticulates) with or without 10 mM methionine and 0.02% polysorbate-80 and incubated at 4° C., 25° C., and 40° C. in HDPE bottles for 2 months. Multiparticulates were crushed and extracted overnight using a 100 mM sodium phosphate, 300 mM glycine, 0.02% polysorbate-80, 10 mM methionine, pH 7.0 buffer at ambient temperature on a flatbed gel shaker set at low speed. Samples were analyzed periodically by reversed-phase HPLC.

The stability results for rhIL-11 multiparticulates incubated at 40° C. by RP-HPLC for detecting percent (%) oxidized methionine[58] species in formulations with and without methionine and polysorbate-80 were compared. The samples were injected onto a poros R1/H column (4.6 mm ID×100 mm L) that was incubated at 40° C. at a load of 8 μg. The mobile phase was 0.1% TFA in water with a linear gradient of acetonitrile. This method was run on a Waters Alliance HPLC system detecting at 214 nm.

In summary, the addition of 10 mM methionine and 0.02% polysorbate-80 to the rhIL-11 multiparticulate formulation reduces the amount of methionine[58] oxidation. This confirms that methionine benefits the rhIL-11 formulation as an antioxidant.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A composition comprising about 1 µg/ml to about 20 mg/ml IL-11, 100 to about 400 mM glycine and 0.5 to about 2.0% wt/wt cryoprotectant, wherein said IL-11 in said composition shows reduced aggregation as compared to IL-11 stored in a composition with glycine and without said cryoprotectant.

2. The composition of claim 1, where said cryoprotectant is sucrose.

3. The composition of claim 2, where said sucrose is present at a concentration of about 1.0% (wt/wt).

4. The composition of claim 2, comprising about 1 to about 5 mg/ml IL-11, about 300 mM glycine, and about 1% sucrose (wt/wt).

5. The composition of claim 1, where said glycine is present at about 300 mM.

6. The composition of claim 1, further comprising a polysorbate.

7. The composition of claim 6, wherein said polysorbate is polysorbate-20.

8. The composition of claim 6, wherein said polysorbate is present at a concentration of about 0.005 to about 0.1% (wt/vol).

9. The composition of claim 6, wherein said polysorbate is present at a concentration of about 0.02% (wt/vol).

10. The composition of claim 6, comprising about 1 to about 5 mg/ml IL-11, about 300 mM glycine, about 1% sucrose (wt/wt), and about 0.02% polysorbate (wt/vol).

11. The composition of claim 1, further comprising an antioxidant.

12. The composition of claim 11, wherein said antioxidant is L-methionine.

13. The composition of claim 12, wherein said L-methionine is present at a concentration of about 1 to about 100 mM.

14. The composition of claim 12, wherein said L-methionine is present at a concentration of about 10 mM.

15. The composition of claim 12, comprising about 1 to about 5 mg/ml IL-11, about 300 mM glycine, about 1% sucrose (wt/wt), about 0.02% polysorbate (wt/vol), and about 10 mM L-methionine.

16. The composition of claim 15, having a pH of about 7.0.

17. The composition of claim 1, further comprising a buffering agent.

18. The composition of claim 17, wherein said buffering agent maintains the pH of said composition in the range of from about 6.0 to about 8.0.

19. The composition of claim 17, wherein said buffering agent maintains the pH of said composition at about 7.0.

20. The composition of claim 17, wherein said buffering agent is sodium phosphate.

21. The composition of claim 1, where said IL-11 is present at a concentration of about 1 µg/ml to about 20 mg/ml.

22. The composition of claim 1, where said IL-11 is present at a concentration of about 1 to about 5 mg/ml.

23. The composition of claim 1, wherein said composition is lyophilized.

24. The composition of claim 1, wherein the amino acid sequence of said IL-11 comprises amino acids 23–119 of human IL-11.

* * * * *